(12) United States Patent
Wibowo et al.

(10) Patent No.: US 8,696,547 B2
(45) Date of Patent: Apr. 15, 2014

(54) SYSTEM AND METHOD FOR DETERMINING AIRWAY DIAMETER USING ENDOSCOPE

(75) Inventors: Henky Wibowo, Cupertino, CA (US); Jason David Gibbs, State College, PA (US)

(73) Assignee: Broncus Medical, Inc., Mountain View, CA (US)

( * ) Notice: Subject to any disclaimer, the term of this patent is extended or adjusted under 35 U.S.C. 154(b) by 637 days.

(21) Appl. No.: 12/884,735

(22) Filed: Sep. 17, 2010

(65) Prior Publication Data

US 2011/0065982 A1    Mar. 17, 2011

Related U.S. Application Data

(60) Provisional application No. 61/243,310, filed on Sep. 17, 2009.

(51) Int. Cl.
*A61B 1/04* (2006.01)
*A61B 1/00* (2006.01)
*A61B 1/06* (2006.01)
*A61B 5/05* (2006.01)

(52) U.S. Cl.
USPC ............ 600/109; 600/117; 600/160; 600/587

(58) Field of Classification Search
USPC .................. 600/101, 160, 109, 118, 587, 424
See application file for complete search history.

(56) References Cited

U.S. PATENT DOCUMENTS

| | | | | |
|---|---|---|---|---|
| 2005/0010138 | A1* | 1/2005 | Mangiardi et al. | 600/587 |
| 2006/0155217 | A1* | 7/2006 | DeVore et al. | 600/587 |
| 2007/0142705 | A1* | 6/2007 | Ohnishi et al. | 600/109 |
| 2008/0243142 | A1* | 10/2008 | Gildenberg | 606/130 |
| 2008/0269596 | A1* | 10/2008 | Revie et al. | 600/424 |
| 2010/0204547 | A1* | 8/2010 | Tanaka et al. | 600/145 |
| 2012/0041291 | A1* | 2/2012 | Ferren et al. | 600/365 |

OTHER PUBLICATIONS

PCT International Search Report and Written Opinion of the International Searching Authority, issued Apr. 27, 2011, Application No. PCT/US2010/049313.

* cited by examiner

*Primary Examiner* — Philip R Smith
*Assistant Examiner* — William Chou
(74) *Attorney, Agent, or Firm* — Convergent Law Group LLP; Rick Batt

(57) ABSTRACT

A method and system for use with an endoscopic instrument determines anatomical properties of body lumen at various states. Lumen properties such as lumen diameter are identified in two or more states corresponding to, for example, an inflated or deflated state. The lumen states are registered with one another and the anatomical properties are identified in real time at the location of an endoscope or endoscopic instrument used with the endoscope. In one embodiment a diametrical range of an airway is identified in real time at the location of a bronchoscope.

18 Claims, 4 Drawing Sheets

SYSTEM AND METHOD FOR DETERMINING AIRWAY DIAMETER USING ENDOSCOPE

CROSS REFERENCE TO RELATED APPLICATIONS

This application claims priority to provisional application No. 61/243,310 filed Sep. 17, 2009 and entitled "System and Method For Determining Airway Diameter Using Endoscope".

BACKGROUND OF THE INVENTION

Endoscopy is a minimally invasive medical procedure that allows a physician to interrogate the interior of the body through an endoscope, which provides a light source to illuminate the anatomy and a method for viewing the anatomy. Typically, the endoscope includes a set of fiber optic bundles connected to a viewing lens or a camera that provides video output. Examples of endoscopes include colonoscopes for examination and therapeutic use in the colon and bronchoscopes for the trachea and branching airways in the lungs. Such devices allow physicians to reach deep into the body through natural orifices, minimizing the trauma that would be required if more invasive procedures were performed.

Endoscopic procedures are often performed in conjunction with the analysis of medical images, either through the doctor's mental assessment or in computer-aided analysis of the images. Such image analysis is useful as the physician may be limited in their viewing ability by the endoscope, or to minimize procedure times by directing physicians to a certain diagnostic region of interest. Examples of medical images are those produced by fluoroscopy, computed tomography (CT), or magnetic resonance imaging. Such imaging allows the physician to discern parts of the anatomy that may not be viewable during the endoscopic procedure. For instance, in transthoracic needle biopsy, a needle is placed through a bronchoscope to sample the lymph nodes, which are located extraluminally, or beyond airway walls and thus out of the possibility of direct visualization. A CT scan is routinely used to determine the location of lymph nodes relative to the airways that are to be sampled. Such lymph node samples are important for the diagnosis and staging of lung cancer.

Imaging analysis is also useful to identify dimensions of anatomies such as the diameter of an airway. This information is useful in certain procedures such as, for example, determining a size of a tracheal bronchial stent to be in the trachea, or the size of an endotrachial valve to be placed in a segmental bronchial lumen. The determination, however, is complicated by a number of factors including the tidal motion of the lungs, i.e., inhalation and expiration of the lungs modifies the dimension of the lumens. Additionally, the dimension may vary along the length of the lumen.

Despite the availability of some of the known image analysis techniques, a method and system for obtaining the dimension information at a particular location in real time is desired.

SUMMARY OF THE INVENTION

A method for determining properties of a body lumen with an endoscopic instrument includes determining a plurality of sets of properties along the lumen. The sets of properties may correspond to the lumen in a plurality of states. The plurality of sets of properties are registered to one another along the lumen. The method further estimates a location of the instrument relative to the lumen and identifies properties of the lumen at the location of the instrument. For example, the instrument may be a bronchoscope and the body lumen may be an airway, with the diameter of the airway being the property that is determined.

The method may further comprise selecting at least a portion of a length of the body lumen and calculating the volumes of the lumen in the various states. The plurality of states may include a first and second state corresponding to the lumen in an inflated and deflated state. Additionally, the method comprises estimating a third set of properties along the lumen. Estimating a third set of third properties along the lumen may be based on the first and second sets of properties, or may correspond to the lumen at a separate state. The method may include identifying and or displaying the sets of properties.

The method may additionally include the step of deploying an implant in the lumen based on the above referenced identifying step. The implant may include an implant dimension associated with the sets of properties. The lumen may be a trachea, the property being an inner diameter, and the implant being a tracheal stent. Prior to deploying the implant, the method may include selecting a tracheal stent from a plurality of stents having different sizes based on the sets of identified properties.

The invention may utilize a real endoscope, with the property identification being performed during surgery in real time. The properties may also be derived from segmented 3D model data arising from CT scans of the body lumen. The step of estimating the location of the endoscope may be carried out using an image to image based registration approach. This estimating step may be performed prior to, or subsequent to, the registering step.

A system is also disclosed for determining properties of a body lumen with an endoscopic instrument. The system comprises a processor operative to: determine a plurality of sets of properties along the lumen; register the properties to one another along the lumen; estimate a location of the instrument relative to the lumen; and identify at least one property corresponding to the location of the instrument in the lumen. The instrument may be a real endoscope. The system may further comprise an implant and an implant delivery instrument. The implant has a dimension associated with properties identified by the system. In one embodiment, the property is a diameter.

The description, objects and advantages of the present invention will become apparent from the detailed description to follow, together with the accompanying drawings. The disclosure and invention specifically include combination of features of various embodiments as well as combinations of the various embodiments where possible.

DETAILED DESCRIPTION OF THE INVENTION

Figure 1:
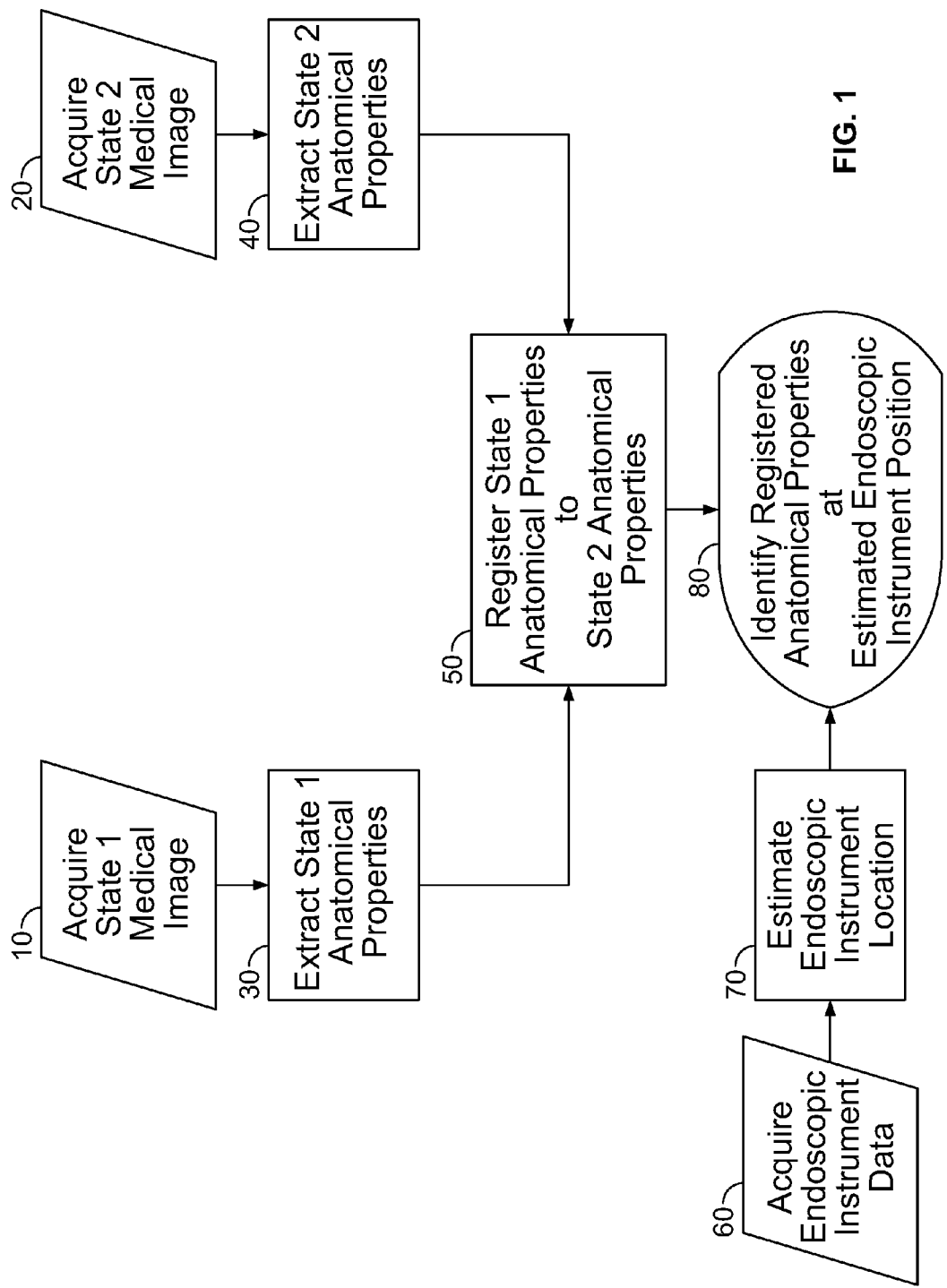
FIG. 1 illustrates the steps of an embodiment of the invention.

A minimally invasive method and system for determining various properties of a body lumen, e.g., an airway, is described herein. FIG. 1 shows an embodiment of the present invention including a sequence of image processing and registration steps to identify one or more anatomical properties of the body lumen at a specific location during an endoscopic procedure. In particular, and as explained in more detail below, one embodiment of the invention includes: (1) acquiring medical image data of a lumen while in at least two different states; (2) segmenting the lumen from the image data; (3) determining anatomical properties of the lumen in each state; (3) registering the anatomical properties corresponding to the lumen in the first state to the anatomical properties corresponding to the lumen in the second state; (4) estimating a location of the endoscope; and (5) identifying the properties of the lumen in the first state and the second state corresponding to the location of the endoscope.

Acquire Medical Image Data

As described above, and with reference to FIG. 1, a first step is acquiring medical image data of the body lumen while the lumen is in different states 10, 20. For the specific case of imaging the chest for a bronchoscopic procedure, the modality is typically computed tomography (CT). However, other imaging modalities such as magnetic resonance imaging (MRI) or positron emission tomography (PET) could be employed to depict the anatomy in the varying states. Still other imaging modalities may be employed and are part of the present invention.

Figure 3A:
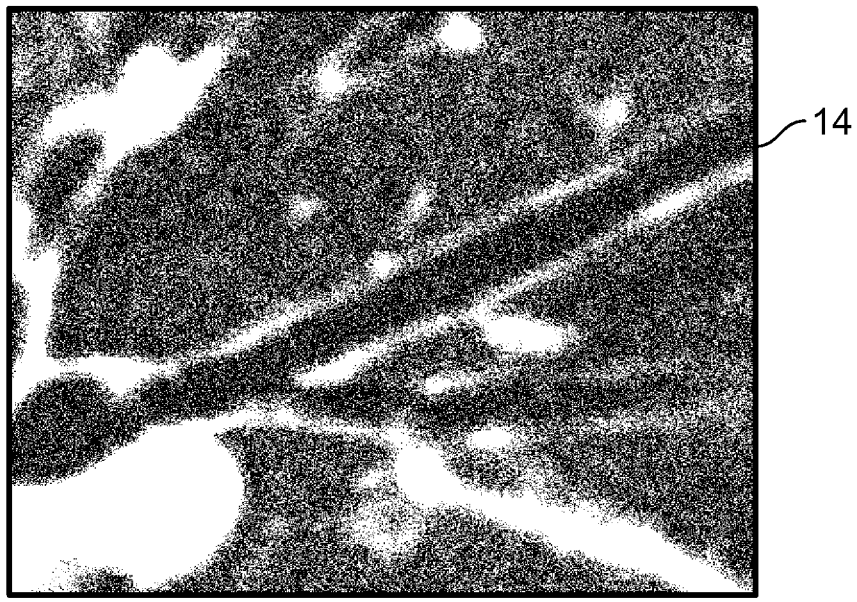
FIGS. 3A and 3B illustrate an oblique CT slice of registered airway lumens in two different states including an inflated state and a deflated state, respectively.
Figure 3B:

FIGS. 3A-3B show CT chest scans of one airway in two different states. FIG. 3A shows the airway in an inflated first state 14. In this embodiment, the inflated airway 14 was acquired at total lung capacity, with the subject holding as much air as possible within the lungs.

FIG. 3B shows the airway in a deflated second state 24. In this embodiment, the deflated airway 24 was acquired at residual volume, with the patient trying to expel as much air as possible from the lungs. Although two different states are described, the invention is not so limited. The airway or body lumen may be imaged and analyzed at additional (e.g., 3rd, 4th, 5th etc.) states as desired. Also, the state of the lumen may vary greatly. In one embodiment of the present invention, as described above, the first state is an inflated state. This first state may be one of full inflation or less. Indeed, the state may be selected based on the desirable measurements to be obtained.

Segment Body Lumens

Figure 2:
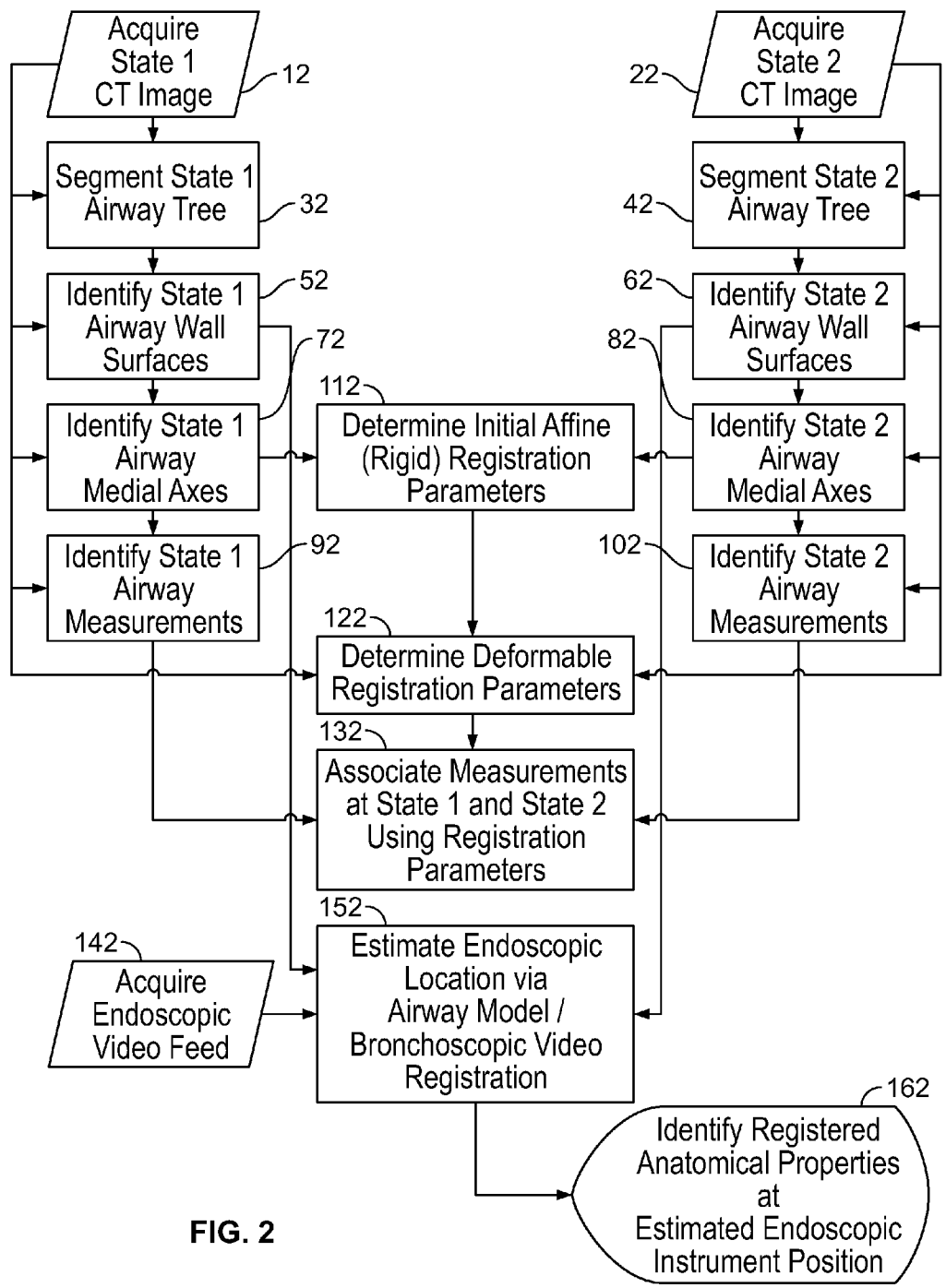
FIG. 2 illustrates the steps of another embodiment of the invention.

Subsequent to acquiring the image data of the lumen in two different states, the lumens must be extracted from other structures in the images. FIG. 2 shows, amongst other things, a set of image processing steps to model the airway tree as described by Gibbs et al, "3D MDCT-Based System for Planning Peripheral Bronchoscopic Procedures," Computers in Biology and Medicine, 2009. Though reference is made to this algorithm to model the airway tree, other techniques may be used in connection with the present invention to generate a model of the body lumen.

With reference to FIG. 2, the airway tree model consists of various components, the first of which is a segmentation of the above described image data. These steps are shown as step 32 and step 42 corresponding to segmentation of the airway in the first state and the airway in the second state respectively. The airway-tree segmentation identifies the set of voxels in the CT scan belonging to the airway tree lumen. There have been various approaches described in the literature for generating airway-tree segmentations from CT scans, including the approach by Vining et al. in U.S. Pat. No. 7,149,564, Summers et al. in U.S. Pat. No. 6,246,784, or Vaz et al. in U.S. patent application Ser. No. 11/299,571, Graham et. al in "Robust System for Human Airway-Tree Segmentation", SPIE Medical Imaging 2008: Image Processing, pp 69141J-1-69141J-18, Tschirren et al. in "Intrathoracic Airway Trees: Segmentation and Airway Morphology Analysis from Low-Dose CT Scans," in IEEE Transactions on Medical Imaging, 2005, pp 1529-1539, and Preteux et al. in "Modeling, Segmentation, and Caliber Estimation of Bronchi in High-Resolution Computerized Tomography," Journal of Electronic Imaging, 1999, pp 36-45.

From the airway tree segmentations at a first state and a second state and the chest CT scans, polygonal airway-wall mesh surfaces of the interface between air and the airway tissue are identified for the anatomy at the first state 52 and the second state 62. The polygonal mesh provides a higher fidelity representation of airway tree when compared to the airway-tree segmentation when the vertices of the mesh polygons are placed with sub-voxel precision. Sub-voxel mesh vertex placement algorithms typically rely upon the partial volume averaging phenomena, which is observable in CT voxels containing disjoint types of matter (e.g., airway tissue and air). The grayscale value of such voxels is an average of the nominal grayscale value of the matter within the voxel weighted by the volume of the matter. For instance, a voxel half-filled with air at a nominal grayscale value of −1000 Hounsfield Units (HU) and half-filled with water with a nominal grayscale value of 0 HU will have a reconstructed grayscale value of −500 HU. Using the grayscale values of voxels and the relative geometry of voxels in a local neighborhood, a polygonal mesh can quickly be formed via a Marching Cubes algorithm such as that disclosed in Cline et al. in U.S. Pat. No. 4,710,876. More recently, other approaches have been proposed to generate more accurate polygonal airway meshes in the presence of CT imaging noise, and anatomical variation such as in Gibbs et al., "3D MDCT-Based System for Planning Peripheral Bronchoscopic Procedures," Computers in Biology and Medicine, 2009, pp 266-279, Saragaglia et. al, in "Airway wall thickness assessment: A New Functionality in Virtual Bronchoscopy Investigation," SPIE Medical Imaging 2007: Physiology, Function, and Structure from Medical Images, pp. 65110P-1-65110P-12. In accordance with the present invention, the step of identifying or determining the airway wall surfaces may be computed using various methods some of which are described above.

Both the airway-tree segmentation and polygonal surface mesh provide representations of the airway-tree as a whole, but neither provide distinction of the individual airways between the branch point bifurcations. Such topology may be reflected by hierarchical medial axes, which can be extracted from the airway-tree polygonal surface mesh and is shown as step 72 and step 82 of FIG. 2. The medial axes, or airway centerlines, provide a sparse representation of the airway tree and give a natural representation of the bifurcation points; where the airways split, as well as the centerlines. Such centerlines consist of a collection of three-dimensional points within the airways. Each three-dimensional point represents a local cross section of the modeled airway lumen.

The collection of centerline points are typically represented in a data structure referred to as a tree in the computer science literature. The tree is rooted at a proximal trachea location and each individual centerline point—with the exception of the proximal trachea root—has a pointer to its ancestor and possibly to its descendant(s). The ancestor is a point in the airway tree immediately more proximal in location, while the descendants are more distal. The representation of and airway tree in this manner was suggested by Kiraly et al. in "Three-Dimensional Path Planning for Virtual Bronchoscopy," IEEE Transactions on Medical Imaging, 2004, pp 1365-1379. More generally, such a data structure is described by Cormen et al. in the textbook "Introduction To Algorithms, Second Edition," 2001.

Determine Anatomical Properties of the Lumens

Referring to FIG. 2, the model data is analyzed to determine a set of properties of the airways in the first state 92 and second state 102. Examples of properties include but are not limited to measurements, diameter, area, thickness, texture, etc. Although specific reference is made to airways and the bronchial tree, the invention is not so limited. Any suitable lumens may be analyzed including for example the colon, sinuses, urethra, and other lumens.

The properties of the airways are determined 92, 102 based on properties of the CT scan and the components of the airway model. The literature describes a variety of approaches for quantifying the cross-sectional properties of airways which can include the minimum axis diameter, the maximum axis diameter, and cross sectional area. Kiraly et al. in "Virtual Bronchoscopy for Quantitative Airway Analysis," SPIE Medical Imaging 2005: Physiology Function, and Structure from Medical Images, 2005 used the full-width half-maximum (FWHM) approach to determine the airway wall locations in the CT image relative to the centerline locations. In this approach rays are cast in the CT image such that the rays are orthogonal to the running direction of the airway. Interpolated points along the rays are sampled to create a profile of intensity locations in the image. The radiologic appearance of airway lumen is dark, the surrounding airway walls are brighter, and the parenchyma surrounding the airway is typically dark relative to the wall. Therefore, the intensity profile should contain a plateau where the airway wall is located. The FWHM approach identifies the beginning and termination of the plateau, corresponding to the inner and outer location of the airway walls. By sufficiently sampling these locations relative to the centerline location, the two-dimensional profile of surface area and diameters is identified for the inner airway lumen boundary, airway-wall thickness, and outer airway-lumen boundary.

The FWHM CT-based measurements, however, can be corrupted by image noise or distracters, such as blood vessels, that confound the FWHM assumptions. To address these issues, Gibbs in "Three Dimensional Route Planning for Medical Image Reporting and Endoscopic Guidance," Pennsylvania State University Dissertation, 2009, described an approach where the airway-tree segmentation is used in place of the CT to quantify the inner airway measurements. This approach associates cross-sections of the segmentation with the centerlines and analyzes the segmentation cross sections to determine inner airway lumen measurements. At local locations around the centerline locations, the segmentation cross sections are subjected to a principal components analysis to determine the measurements.

Other approaches for airway quantification include making measurements from the polygonal airway surface meshes. For example, cylinders may be generalized on the surface meshes to generate the centerlines, as described by Yu et al. in "System for the Analysis and Visualization of Large 3D Anatomical Trees," Computers in Biology and Medicine, 2007. However, the generalized cylinders—which trace out a curve on the surface mesh around a local airway cross section—can be further analyzed to determine the measurements. Similarly, airway polygonal meshes are used to determine cross sectional airway lumen measurements. Saragaglia et al "Airway Wall Thickness Assessment: A New Functionality in Virtual Bronchoscopy Investigation," SPIE Medical Imaging: Physiology, Function, and Structure from Medical Images, 2007.

Registering the Lumens

Next, as depicted in FIGS. 1-2, the properties of the airway in state 1 and state 2 are registered (50, 132) to one another. The images shown in FIGS. 3A, 3B are examples of an airway registered such that the CT cross sections are computed at the same plane relative to the subject's body. Furthermore the pixels that comprise the images reflect areas within the plane of identical geometric size, with each pixel representing anatomy with dimensions of 0.5 mm×0.5 mm. In this way, the images depicted in FIGS. 3A, 3B are sought to be made identical, with the variation in appearance resulting from the differing breathing levels.

Various approaches exist to register a lumen at one state to the lumen at a second state. One embodiment of the present invention includes a step of registration of the lumens by relating a geometric location in the coordinate system of the lumen in state 1 to a geometric position of the lumen in state 2 such that the underlying part of the anatomy is the same in the two different coordinate systems. This step is useful because the CT scans are typically not aligned with one another. For example, CT at state 1 may begin at a different location on the patient than the CT at state 2, or the patient may have a different level of inspiration in the two scans, which causes the deformable organs within the chest to change position to one another so that a voxel at location (i,j,k) in the first state scan does not correspond to the same portion of the body of the second state CT.

One lumen registration approach consists of directly matching the voxels in the CT scans to one another through a mathematical function under the assumption that the body should have a similar appearance in two different states, but the parts of the body may have shifted in position. The level of accuracy for such registrations can be of a rigid body type consisting of a uniform set of translations and rotations to align all voxels in the first state to the second state (112). Providing more degrees of freedom is an affine registration. Additionally, a deformation field, as described in US 2007/0116381 identifies an individual mapping for voxels within one CT image to a location within the other CT image. Approaches for calculating these deformation fields (122) have been described in "Image matching as a diffusion process: an analogy with Maxwell's demons," Medical Image Analysis, 1998 by J. P. Thirion and "Nonrigid registration using free-form deformations: Application to breast MR images," IEEE Transactions on Medical Imaging 712-721, 1999 by D. Rueckert et al.

Since the centerlines are located within the volumetric image, the rigid-body or affine registrations provide global equations that give the location of a property location in the geometry of the second state. Similarly, the deformation field provides a local mapping at a particular location within the first-state geometry system to a location in the second-state system. With such associations or registrations, if a particular location with associated properties is known in the first state, the location of the same anatomical region can be determined in the geometry of the second state. Since the second-state properties are also associated to locations in the second state, these mappings provide a link between the properties in the two geometric systems. More concretely, the finely sampled centerline locations in the first state are mapped to the finely sampled centerline locations derived from the airways in the second state such that the associations "line up" the same anatomical regions in the centerlines of the two different states. That is, if a centerline point p1 is in the middle of a particular airway, for instance the trachea, it would map to a centerline point p2 in the second state centerlines that is also in the middle of the trachea.

A second approach for registering the lumens to one another can be made using specific parts of the airway models, e.g., the centerlines. In this approach, the points on the airway model are matched to one another, giving a one-to-one mapping of a subset of the points in the state 1 centerlines to a subset of the points in the state 2 centerlines. Examples of such an approach include U.S. patent application Ser. No. 11/122,974 by Tschirren et al., and U.S. patent application Ser. No. 11/673,621 by Kiraly et al. With the model points in the respective states associated to the lumen properties in the respective states, the mapping between the points in the two models provides a mapping of properties at locations in space.

Estimate Location of Endoscope

Estimating the location of the endoscope may be carried out using various techniques. One example of estimation the location of the endoscope includes registering the endoscope with the model data in a particular state as described in U.S. patent applications Nos. 11/437,229; and 11/437,230, both to Higgins et al. In this method the location of the bronchoscope is determined relative to at least one of the following: the coordinate system of the model in state 1, the coordinate system of the model in state 2.

In particular, in the '229 patent application a method provides guidance to the physician during a live bronchoscopy or other endoscopic procedures. The 3D motion of the bronchoscope is estimated using a fast coarse tracking step followed by a fine registration step. The tracking is based on finding a set of corresponding feature points across a plurality of consecutive bronchoscopic video frames, then estimating for the new pose of the bronchoscope. In the preferred embodiment the pose estimation is based on linearization of the rotation matrix. By giving a set of corresponding points across the current bronchoscopic video image, and the CT-based virtual image as an input, the same method can also be used for manual registration. The fine registration step is preferably a gradient-based Gauss-Newton method that maximizes the correlation between the bronchoscopic video image and the CT-based virtual image. The continuous guidance is provided by estimating the 3D motion of the bronchoscope in a loop. Since depth-map information is available, tracking can be done by solving a 3D-2D pose estimation problem. A 3D-2D pose estimation problem is more constrained than a 2D-2D pose estimation problem and does not suffer from the limitations associated with computing an essential matrix. The use of correlation-based cost, instead of mutual information as a registration cost, makes it simpler to use gradient-based methods for registration.

In the '230 patent application a novel framework for fast and continuous registration between two imaging modalities is disclosed. The approach makes it possible to completely determine the rigid transformation between multiple sources at real-time or near real-time frame-rates in order to localize the cameras and register the two sources. A disclosed example includes computing or capturing a set of reference images within a known environment, complete with corresponding depth maps and image gradients. The collection of these images and depth maps constitutes the reference source. The second source is a real-time or near-real time source which may include a live video feed (60, 142). Given one frame from this video feed, and starting from an initial guess of viewpoint, the real-time video frame is warped to the nearest viewing site of the reference source. An image difference is computed between the warped video frame and the reference image. The viewpoint is updated via a Gauss-Newton parameter update and certain of the steps are repeated for each frame until the viewpoint converges or the next video frame becomes available. The final viewpoint gives an estimate of the relative rotation and translation between the camera at that particular video frame and the reference source. The invention has far-reaching applications, particularly in the field of assisted endoscopy, including bronchoscopy and colonoscopy. Other applications include aerial and ground-based navigation.

Another example of estimating the location of the endoscope is discussed in U.S. Pat. No. 6,593,884 to Gilboa. In the '884 Patent, a method and system for tracking a probe such as a catheter is shown having three at least partly overlapping planar antennas used to transmit electromagnetic radiation simultaneously, with the radiation transmitted by each antenna having its own spectrum. A receiver inside the probe includes sensors of the three components of the transmitted field, with sensors for at least two of the three components being pairs of sensors, such as coils, on opposite sides of a common reference point. The position and orientation of the receiver relative to the antennas are determined.

The endoscope estimating step may be performed in real time or not. Additionally, the endoscope estimating step may be performed prior to or subsequent to the above described lumen registration or mapping step. In one embodiment of the present invention the step of estimating the location of the endoscope 70, 152 is carried out live or in real time and subsequent to the lumen registration step. As used herein, by "real time" it is meant about 30 frames per second or faster, allowing for the position of the location of the endoscopic instrument to be determined at a rate consistent with the refresh rate of bronchoscopic video feed as displayed on a video monitor. The image to image registration described in U.S. patent application Ser. Nos. 11/437,229 and 11/437,230 to Higgins et al. achieve video frame rates on commercially-available desktop computers.

The endoscopic instrument estimating step 70, 152 may also be applicable to devices used in combination with an endoscope. It is well established that commercially available endoscopes contain working channels through which a number of clinical devices, such as needles, forceps, probes, catheters, brushes, and positional sensors can be inserted. The present invention is applicable and specifically includes estimating the location of the endoscope itself, and estimating the location devices or accessories used in combination with the endoscope such as but not limited to the instruments described above.

Identify Properties

Subsequent to estimating the location of the endoscope, and registering the lumen in two or more different states, at least one property is identified (80, 162) at the location of the endoscope. The one or more properties are identified by retrieving or "looking up" the stored properties at the location of the endoscope from the lumen model. At any given location along the airway, for instance, the properties derived from the first state, second state, and other states may be obtained. Additionally, a third property may be identified based on the first property and the second property by, for example, averaging or interpolating between the first property and the second property at the selected or estimated location. A real-time estimate of a property (e.g., real-time diameter) may be provided at the location of the endoscope by, for example, interpolating between the first property and the second property at the endoscope location.

Additionally, the invention may include displaying properties on a display device such as a video monitor, possibly in real time, or storing the properties to a storage medium for retrieval or consumption by other processing devices after the identification(s). In addition, multiple properties, such as diameters and lumen wall thicknesses can be displayed for the lumen at one or more of the states.

The property information identified may be utilized to carry out various procedures including diagnostic and treatment procedures. In one embodiment of the invention, the identified anatomical properties are used to estimate the size of a treatment device (e.g., an ablation catheter, needle, brush, etc.) or an implant. Examples of implants include but are not limited to stents, valves, plugs, occludants, fiducials, etc.

Figure 4:
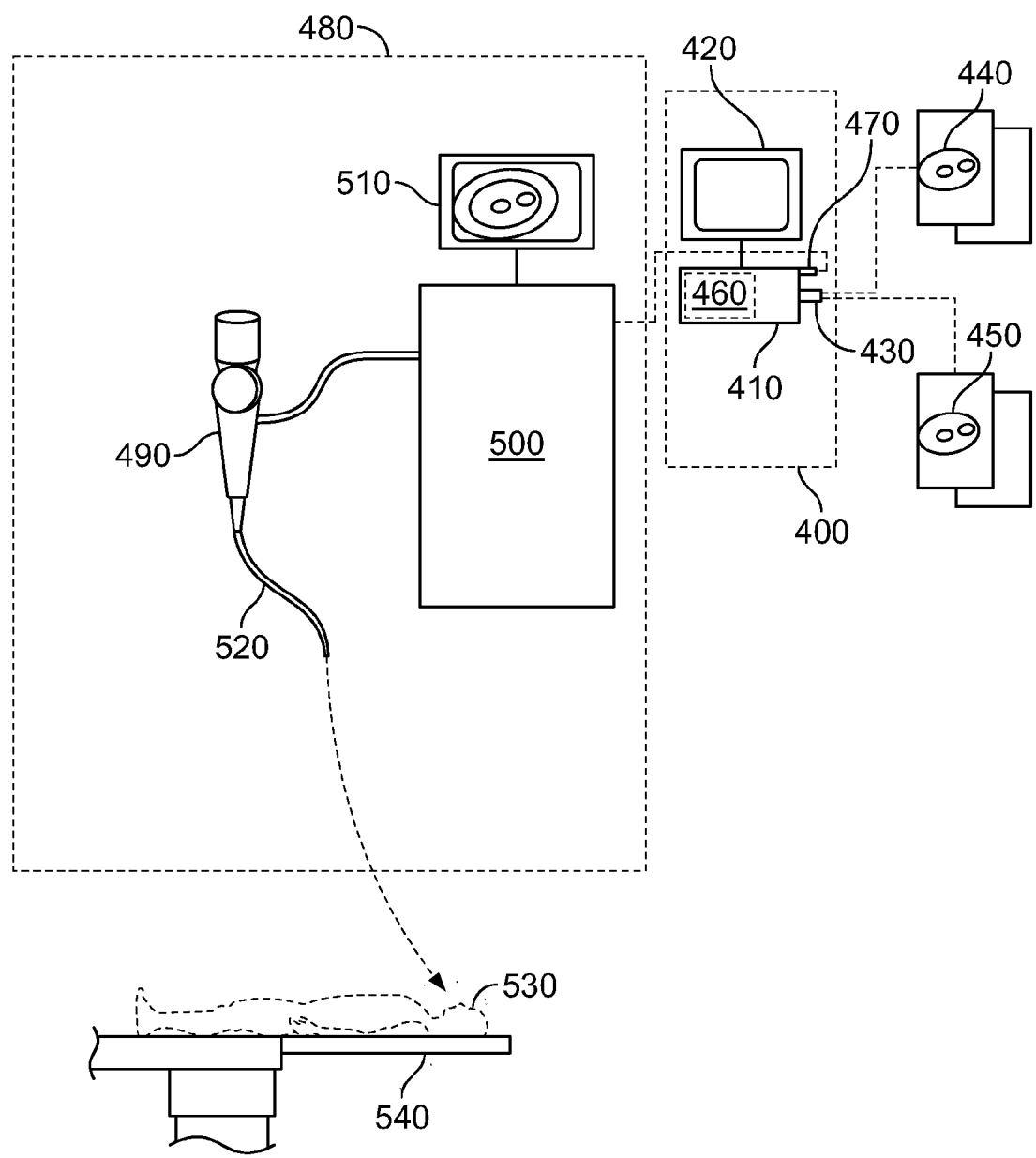
FIG. 4 illustrates a system for carrying out the invention.

As indicated above, and with reference to FIG. 4, the various described steps may be carried out on a system 400. The system includes a computer 410, and display 420. The computer also includes an input 430 for receiving image data in a first state 440 or a second state 450, or additional states as the case may be. A processor 460 in the computer preferably is operative to carry out one or more of the above described steps including, for example, extracting the body lumens and registering the properties of the lumen in the first state to that of the second state.

The system 400 additionally has an instrument input 470 for accepting data or information from an instrument such as an endoscope system 480. The endoscope system includes an endoscope 490, controller 500, and a display or monitor 510. The endoscope typically includes an elongate flexible member 520 that is advanced into the airways of a patient 530 through a natural oral opening such as the nose or mouth positioned on an operating table 540. As described above in connection with step 152 of FIG. 2, the system 400 can estimate the location of the instrument and determines properties of the lumen at the location.

All patents, publications, and patent applications herein are incorporated by reference in their entirety.

We claim:

1. A method for determining properties of a body lumen at different states with an endoscopic instrument comprising: providing a computer having a processor configured to:
    acquire a first set of 3D image data of a body lumen at a first lumen state;
    acquire a second set of 3D image data of the body lumen at a second lumen state, the body lumen having a different shape in the second lumen state than in the first lumen state;
    determine from the first set of previously acquired 3D image data a first property at each location along the body lumen;
    determine from the second set of previously acquired 3D image data the first property at each location along the body lumen;
    register the first property at the first lumen state to the first property at the second lumen state at each location along the body lumen, thereby mapping the first property at the first lumen state and the first property at the second lumen state for each location along the body lumen;
    estimate an endoscopic instrument position of the endoscopic instrument relative to the body lumen when the endoscopic instrument has been advanced into the body lumen; and
    automatically identify in real time at least one of the following: the first property at the first lumen state based on the endoscopic instrument position and the mapping, and the first property at the second lumen state based on the endoscopic instrument position and the mapping.

2. The method of claim 1 wherein said endoscopic instrument is a bronchoscope and said body lumen is an airway.

3. The method of claim 1 wherein said first property is a diameter.

4. The method of claim 3 wherein said first lumen state corresponds to said body lumen being inflated.

5. The method of claim 4 wherein said second lumen state corresponds to the body lumen being deflated.

6. The method of claim 3 further comprising selecting at least a portion of a length of the body lumen and calculating a volume of said body lumen in said first lumen state and the volume of said body lumen in said second lumen state.

7. The method of claim 1 further comprising deploying an implant in said body lumen, said implant having an implant dimension associated with said at least one of the first property at the first lumen state and the first property at the second lumen state.

8. The method of claim 7 wherein said body lumen is a trachea, said first property is an inner diameter, and said implant is a tracheal stent, and further comprising, prior to said deploying step, a step of selecting the tracheal stent from a plurality of stents having different sizes based on said first property.

9. The method of claim 1 further comprising displaying said at least one first property at the first lumen state, and the first property at the second lumen state.

10. The method of claim 1 further comprising estimating the first property at each location along the body lumen at a third lumen state wherein said first property of the body lumen at the third lumen state is based on at least one of the first property of the body lumen at the first lumen state and the first property of the body lumen at the second lumen state.

11. The method of claim 1 further comprising identifying said first property.

12. The method of claim 1 wherein said endoscopic instrument is a real endoscope, and said identify step is performed in real time.

13. The method of claim 1 wherein said first property at each location along the body lumen at the first lumen state is derived from segmented 3D model data arising from CT scans of the body lumen.

14. The method of claim 1 wherein the estimate step is carried out by registering the endoscopic instrument position to the body lumen.

15. The method of claim 14 wherein said registering the endoscopic instrument location to the body lumen is carried out using an image to image based registration approach.

16. The method of claim 1 wherein the estimate step is performed prior to the register step.

17. The method of claim 1 further comprising estimating the first property of the body lumen at a third lumen state at the endoscopic instrument position and based on said at least one of the first property at the first lumen state, and the first property at the second lumen state.

18. The method of claim 1 wherein the endoscopic instrument is an endoscope and the method further comprises receiving video from said endoscope.

* * * * *